United States Patent
Tanaka et al.

(10) Patent No.: US 7,569,100 B2
(45) Date of Patent: Aug. 4, 2009

(54) AIR PURIFICATION DEVICE

(75) Inventors: Toshio Tanaka, Osaka (JP); Kanji Motegi, Osaka (JP); Kenkichi Kagawa, Osaka (JP); Mitsuhisa Nagao, Shiga (JP); Kiyohito Hamaguchi, Shiga (JP); Tomoharu Tanzo, Shiga (JP)

(73) Assignee: Daikin Industries, Ltd., Osaka-shi, Osaka (JP)

( * ) Notice: Subject to any disclaimer, the term of this patent is extended or adjusted under 35 U.S.C. 154(b) by 402 days.

(21) Appl. No.: 10/592,353

(22) PCT Filed: Mar. 18, 2005

(86) PCT No.: PCT/JP2005/004982

§ 371 (c)(1),
(2), (4) Date: Sep. 11, 2006

(87) PCT Pub. No.: WO2005/089908

PCT Pub. Date: Sep. 29, 2005

(65) Prior Publication Data

US 2007/0193448 A1 Aug. 23, 2007

(30) Foreign Application Priority Data

Mar. 18, 2004 (JP) .............................. 2004-078378

(51) Int. Cl.
*B03C 3/68* (2006.01)
(52) U.S. Cl. ............................ 96/18; 95/2; 95/3; 96/19; 96/63
(58) Field of Classification Search ...................... 96/18, 96/19, 63; 95/2, 3, 78
See application file for complete search history.

(56) References Cited

U.S. PATENT DOCUMENTS

| 3,996,474 | A | | 12/1976 | Lowther |
| 4,284,417 | A | * | 8/1981 | Reese et al. ...................... 95/3 |
| 4,613,346 | A | * | 9/1986 | Reyes et al. ...................... 95/3 |
| 4,624,685 | A | * | 11/1986 | Lueckenotte et al. ............. 95/3 |
| 5,035,728 | A | * | 7/1991 | Fang .............................. 96/19 |
| 5,154,734 | A | * | 10/1992 | Yung .............................. 95/8 |
| 5,688,308 | A | * | 11/1997 | Voigts ............................ 96/18 |
| 5,759,487 | A | | 6/1998 | Jung et al. |
| 6,040,777 | A | * | 3/2000 | Ammann et al. ............. 340/632 |
| 6,245,131 | B1 | * | 6/2001 | Rippelmeyer et al. .......... 96/18 |
| 6,312,507 | B1 | * | 11/2001 | Taylor et al. ................... 96/19 |
| 6,375,714 | B1 | * | 4/2002 | Rump et al. ...................... 95/3 |
| 6,623,544 | B1 | * | 9/2003 | Kaura ............................. 95/3 |
| 6,660,061 | B2 | * | 12/2003 | Josephson et al. ................. 95/2 |
| 7,270,698 | B2 | * | 9/2007 | Tanaka et al. .................. 96/95 |
| 7,332,020 | B2 | * | 2/2008 | Tanaka et al. .................. 96/66 |
| 7,377,962 | B2 | * | 5/2008 | Tanaka et al. .................. 96/83 |

(Continued)

FOREIGN PATENT DOCUMENTS

DE 43 34 956 A1 4/1995

(Continued)

*Primary Examiner*—Richard L Chiesa
(74) *Attorney, Agent, or Firm*—Birch, Stewart, Kolasch & Birch, LLP

(57) ABSTRACT

An electric power supply of a discharge device which generates a streamer discharge is provided with a discharge control part. By virtue of the discharge control part, the discharge electric power of the discharge device is increased or decreased depending on the treatment amount of a component to be treated in an air purification device.

4 Claims, 11 Drawing Sheets

U.S. PATENT DOCUMENTS

2002/0014401 A1    2/2002  Fleischer
2007/0193448 A1*   8/2007  Tanaka et al. .................. 96/18

FOREIGN PATENT DOCUMENTS

| EP | 0 770 337 A2 | 5/1997 |
| EP | 1 125 588 A2 | 8/2001 |
| GB | 2110431 A * | 6/1983 | ..................... 95/3 |
| JP | 11-57387 A | 3/1999 |
| JP | 2000-135281 A | 5/2000 |
| JP | 2001-218828 A | 8/2001 |
| JP | 2001-259009 A | 9/2001 |
| WO | WO-2004/014442 A1 | 2/2004 |

* cited by examiner

FIG. 5

| OPERATION | AIR VOLUME [m³/min] | DISCHARGE CURRENT [μA] |
|---|---|---|
| A | 6.0 | 37 |
| B | 3.5 | 37 |
| C | 2.7 | 37 |
| D | 1.9 | 5.5 |
| E | 0.9 | 5.5 |

FIG. 7

| OPERATION | AIR VOLUME [m³/min] | DISCHARGE CURRENT [μA] |
|---|---|---|
| A | 6.0 | 37 |
| B | 3.5 | 37 |
| C | 2.7 | 37 |
| D | 1.9 | OFF |
| E | 0.9 | OFF |

FIG. 8

| OPERATION | AIR VOLUME [m³/min] | DISCHARGE CURRENT [μA] |
|---|---|---|
| A | 6.0 | 37 |
| B | 3.5 | 30 |
| C | 2.7 | 20 |
| D | 1.9 | 10 |
| E | 0.9 | 5.5 |

FIG. 11

| OPERATION | AIR VOLUME [m³/min] | DISCHARGE CURRENT OF FIRST DISCHARGE DEVICE [μA] | DISCHARGE CURRENT OF SECOND DISCHARGE DEVICE [μA] |
|---|---|---|---|
| A | 6.0 | 37 | 37 |
| B | 3.5 | 37 | 37 |
| C | 2.7 | 37 | 37 |
| D | 1.9 | 37 | OFF |
| E | 0.9 | 37 | OFF |

AIR PURIFICATION DEVICE

This application is a national stage application of International Application No. PCT/JP05/04982 filed on Mar.18, 2005.

TECHNICAL FIELD

The present invention relates to an air purification device, capable of decomposing a component to be treated that is contained in a stream of air to be treated, which includes a discharge device for generating a streamer discharge.

BACKGROUND ART

An air purification device which is equipped with a discharge device has been used as a means for decomposing and removing, by a plasma generated by electric discharge, components (such as odorous components, harmful components, and other contaminants) to be treated that are contained in a stream of air to be treated. One such purification device is an air purification device of the streamer discharge type in which a low temperature plasma is produced by streamer discharge and which is regarded as a preferable technology for decomposing and deodorizing harmful components because it can provide higher air purification efficiency in comparison with air purification devices of other discharge types (for example, glow discharge type air purification devices and corona discharge type air purification devices).

With reference to FIG. 13, there is shown a typical streamer discharge type air purification device which includes, as a discharge device (80), discharge electrodes (81) and counter electrodes (82) facing the discharge electrodes (81). The discharge electrodes (81) are arranged in parallel at predetermined intervals on a substrate (83). Each discharge electrode (81) is formed such that it has a projecting tip. On the other hand, the counter electrodes (82) are arranged at predetermined intervals on both sides of the substrate of the discharge electrodes (81). And the tips of the discharge electrodes (81) and the counter electrodes (82) are positioned face to face with each other. In addition, the air purification device further includes an electric power supply means (not shown) configured to apply voltages to both the electrodes (81, 82) and an air blower means (not shown) by which a stream of air to be treated is distributed to the discharge device (80). In this configuration, when the air blower means is activated and the electric power supply means applies voltages to both the electrodes (81, 82), a streamer discharge is generated between both the electrodes (81, 82), thereby generating a low temperature plasma. Components contained in a stream of air to be treated are brought into aeration contact with activated species (fast electron, ion, radical, other excited molecule et cetera) produced as a result of generation of the low temperature plasma, whereby these components to be treated are decomposed and removed from the air stream (see Patent Document I).

Patent Document I: JP 2001-218828A

DISCLOSURE OF THE INVENTION

Problems That the Invention Intends to Solve

Incidentally, in a streamer discharge type air purification device as disclosed in Patent Document I, it is required that high voltages be applied to both the discharge electrode (81) and the counter electrode (82) at the time of streamer discharge, in other words relatively large amounts of electric power are consumed. Here, for example, as the concentration of odorous and harmful components in an indoor space where the air purification device is installed becomes thinner, the treatment amount of the component to be treated by the air purification device decreases. Accordingly, the treatment capability of the air purification device obtained by streamer discharge exceeds the treatment amount of the component to be treated, and energy that is consumed at the time of streamer discharge may be wasted.

With a view to providing solutions to the above-described problems, the present invention was devised. Accordingly, an object of the present invention is to inhibit wasteful consumption of discharge electric power when the treatment capability becomes excessive relative to the treatment amount of the component to be treated at the time of streamer discharge, whereby the air purification device can be improved in its energy saving properties.

Means for Solving the Problems

In the present invention, the discharge electric power of a discharge device (40) is increased or decreased depending on the treatment amount of a component to be treated.

More specifically, a first invention is directed to an air purification device which comprises: a discharge device (40) for generating a streamer discharge between a discharge electrode (41) and a counter electrode (42) facing the discharge electrode; an electric power supply means (45) for applying voltages to both the electrodes (41, 42); and an air blower means (26) for distributing to the discharge device a stream of air to be treated, wherein the air purification device is capable of decomposing, by the streamer discharge, a component to be treated which is contained in the air stream to be treated. The air purification device of the first invention is characterized in that it further includes a discharge control part (63) for increasing or decreasing the discharge electric power of the discharge device (40) depending on the air volume of the air blower means (26).

In the first invention, upon voltage application to the discharge device (40) from the electric power supply means (26), a streamer discharge is generated between the discharge electrode (41) and the counter electrode (42) at a predetermined discharge electric power level. As a result, with the generation of a low temperature plasma, the above-described activated species are generated. And the component to be treated which is contained in the air stream to be treated is oxidation-decomposed by the activated species, whereby the air stream to be treated is cleaned and purified.

Here, in this invention, the electric power supply means (45) is provided with the discharge control part (63). And by virtue of the discharge control part (63), the discharge electric power of the discharge device (40) is increased or decreased depending on the air volume of the air blower means (26). Consequently, for example, when performing an operation in which the air volume of the air blower means (26) is switched to a higher air volume level because in the indoor space where the air purification device is installed the concentration of the component to be treated becomes higher, the generation amount of the activated species can be increased by increasing the discharge electric power by a predetermined amount. This therefore makes it possible to generate activated species in an amount depending on the treatment amount of the component to be treated, whereby the air stream to be treated is efficiently cleaned and purified.

On the other hand, for example, when performing an operation in which the air volume of the air blower means (26) is switched to a lower air volume level because in the indoor space the concentration of the component to be treated becomes lower, the generation amount of the activated species can be decreased by decreasing the discharge electric power by a predetermined amount. This therefore inhibits the treatment capability obtained by the streamer discharge of the discharge device (40) from becoming excessive relative to the treatment amount of the component to be treated, thereby preventing the discharge electric power from being wasted.

A second invention provides an air purification device according to the first invention which is characterized in that the air purification device further includes an air volume control part (64) for switching the air volume of the air blower means (26) among a plurality of set air volume levels; a plurality of set discharge electric power levels are set to the discharge control part (63); and the discharge control part (63) is configured so that the discharge electric power is switched to each of the plural set discharge electric power levels depending on each of the plural set air volume levels of the air blower means (26). Here, the aforesaid "plural set air volume levels" may be a combination of a set air volume level at which the air volume of the air blower means (26) is zero (the air blower means (26) is turned off) and a set air volume level at which the air volume of the air blower means (26) is at a predetermined value (the air blower means (26) is turned on). In addition, likewise, the aforesaid "plural set discharge electric power levels" may be a combination of a set discharge electric power level at which the discharge electric power of the discharge device (40) is zero (the discharge device (40) is turned off) and a set discharge electric power level at which the discharge electric power of the discharge device (40) is at a predetermined value (the discharge device (40) is turned on). Furthermore, the number of set levels for each of the air volume and the discharge electric power is preferably three or more. In addition, the air volume and the discharge electric power are not necessarily to be identical with each other in the number of set levels, in other words the correspondence between the set air volume level and the set discharge electric power level is not necessarily required. Stated another way, for example, in the case where the number of set levels of the air volume is five (A, B, C, D, and E) while on the other hand the number of set levels of the discharge electric power is two (i.e. a first set discharge electric power level and a second set discharge electric power level), it may be arranged such that the set air volume levels A, B, and C correspond to the first set discharge electric power level, while the set air volume levels D and E correspond to the second set discharge electric power level.

In the second invention, the air volume of the air blower means (26) is switched to each set air volume level by the air volume control part (64), while simultaneously the discharge electric power of the discharge device (40) is switched to each set discharge electric power level depending on the set air volume level.

Here, for example, when the air volume of the air blower means (26) is increased up to a high set air volume level because in the indoor space the concentration of the component to be treated becomes higher, the generation amount of the activated species can be increased by setting the discharge electric power to a high set discharge electric power level depending on the high set air volume. This therefore makes it possible to generate activated species in an amount depending on the treatment amount of the component to be treated, whereby the air stream to be treated is efficiently cleaned and purified.

On the other hand, for example, when the air volume of the air blower means (26) is decreased down to a low set air volume level because in the indoor space the concentration of the component to be treated becomes lower, the generation amount of the activated species can be decreased by setting the discharge electric power to a low set discharge electric power level depending on the low set air volume. This therefore inhibits the treatment capability obtained by the streamer discharge of the discharge device (40) from becoming excessive relative to the treatment amount of the component to be treated, thereby preventing the discharge electric power from being wasted.

A third invention provides an air purification device according to the second invention which is characterized in that the discharge control part is configured so that the discharge electric power is made to change after a set time (t) has elapsed since the air volume of the air blower means was made to change by the air volume control part.

In the third invention, the discharge electric power is made to change after the set time (t) has elapsed since the air volume of the air blower means (26) was made to change. Here, by the provision of the set time (t), it becomes possible to make a change in discharge electric power, with the air volume of the air blower means (26) approaching a set air volume level after the air volume level was made to change. This therefore makes it possible to make a change in discharge electric power, with the treatment amount of the component to be treated being stable.

A fourth invention is directed to an air purification device which comprises: a discharge device (40) for generating a streamer discharge between a discharge electrode (41) and a counter electrode (42) facing the discharge electrode (41); an electric power supply means (45) for applying voltages to both the electrodes (41, 42); and an air blower means (26) for distributing to the discharge device a stream of air to be treated, wherein the air purification device is capable of decomposing, by the streamer discharge, a component to be treated which is contained in the air stream to be treated. The air purification device of the fourth invention is characterized in that it includes a concentration detection means (70) for detecting the concentration of the component to be treated which is contained in the air stream to be treated, and a discharge control part (63) for increasing or decreasing the discharge electric power of the discharge device (40) depending on the concentration detected by the concentration detection means (70). Here, the "concentration detection means" is implemented by a means capable of detecting either the concentration of odorous and harmful components able to be treated by the air purification device or the odor concentration.

In the fourth invention, based on the concentration of the component to be treated which is detected by the concentration detection means (70), the discharge control part (63) increases or decreases the discharge electric power of the discharge device (40).

Here, for example, when the concentration of odorous and harmful components in the indoor space increases and the concentration detection means (70) detects that these components to be treated increase in their concentration, the generation amount of the activated species can be increased by increasing the discharge electric power by a predetermined amount. This therefore makes it possible to generate activated species in an amount depending on the treatment amount of the component to be treated, whereby the air stream to be treated is efficiently cleaned and purified.

On the other hand, for example, when the concentration of odorous and harmful components in the indoor space decreases and the concentration detection means (70) detects that these components to be treated decrease in their concentration, the generation amount of the activated species can be decreased by decreasing the discharge electric power by a predetermined amount. This therefore inhibits the treatment capability obtained by the streamer discharge of the discharge device (40) from becoming excessive relative to the treatment amount of the component to be treated, thereby preventing the discharge electric power from being wasted.

A fifth invention provides an air purification device according to the fourth invention which is characterized in that the air purification device further includes an air volume control part (64) for increasing or decreasing the air volume of the air blower means (26) depending on the concentration detected by the concentration detection means (70).

In the fifth invention, with the increase or decrease in the concentration of the component to be treated detected by the concentration detection means (70), both the air volume of the air blower means (26) and the discharge electric power of the discharge device (40) are increased or decreased.

Here, for example, when performing an operation in which the air volume of the air blower means (26) is switched to a higher set air volume level with the increase in the concentration of the component to be treated, the generation amount of the activated species can be increased by increasing the discharge electric power by a predetermined amount. This therefore makes it possible to generate activated species in an amount depending on the treatment amount of the component to be treated, whereby the air stream to be treated is efficiently cleaned and purified.

On the other hand, for example, when performing an operation in which the air volume of the air blower means (26) is switched to a lower set air volume level with the decrease in the concentration of the component to be treated, the generation amount of the activated species can be decreased by decreasing the discharge electric power by a predetermined amount. This therefore inhibits the treatment capability obtained by the streamer discharge of the discharge device (40) from becoming excessive relative to the treatment amount of the component to be treated, thereby preventing the discharge electric power from being wasted.

Effects of the Invention

In accordance with the first invention, when performing an operation in which the air volume of the air blower means (26) is switched to a higher air volume level, the discharge electric power is increased by a predetermined amount to thereby increase the generation amount of activated species. This therefore makes it possible to generate a streamer discharge at a treatment capability corresponding to the treatment amount of the component to be treated, and the air stream to be treated can be efficiently cleaned and purified.

On the other hand, when performing an operation in which the air volume of the air blower means (26) is switched to a lower air volume level, the discharge electric power is decreased by a predetermined amount to thereby decrease the generation amount of activated species. This therefore inhibits the treatment capability obtained by streamer discharge from becoming excessive relative to the treatment amount of the component to be treated, thereby preventing the discharge electric power from being wasted. Consequently, the air purification device is improved in its energy saving properties.

In addition, in accordance with this invention, when the air volume of the air blower means (26) is switched to a higher air volume level, which turns up the operating sound of the air blower means (26) to a relatively high level, the discharge electric power is increased, so that discharge sounds generated by streamer discharge can be masked by the operating sound of the air blower means (26).

On the other hand, when the air volume of the air blower means (26) is switched to a lower air volume level, which turns down the operating sound of the air blower means (26) to a relatively low level, i.e. when discharge sounds are easily heard by the user, the discharge sounds can be reduced by decreasing the discharge electric power, thereby preventing the discharge sounds from causing discomfort to the user.

In addition, in accordance with this invention, a streamer discharge is generated at a treatment capability corresponding to the treatment amount of the component to be treated. This makes it possible to inhibit the generation of activated species (such as ozone) from becoming excessive relative to the treatment amount of the component to be treated, whereby the emission of unreacted ozone with the component to be treated to outside the device is effectively prevented. Consequently, the air purification device can be improved in its reliability.

In accordance with the second invention, the air volume of the air blower means (26) is made switchable among the set air volume levels. This allows the air purification device to perform its operations capable of meeting indoor space environmental conditions and user operation needs. In addition, the multiple set air volume levels are provided, wherein the air volume of the air blower means (26) is made switchable among the multiple set air volume levels. This enables the air purification device to perform its operations capable of more precisely meeting indoor space environmental conditions and user operation needs.

In addition, in accordance with this invention, the discharge electric power is switched to each set discharge electric power level depending on each set air volume level of the air blower means (26). Accordingly, for example, for the case of an operation in which the air volume of the air blower means (26) is switched to a higher set air volume level, the discharge electric power is set to a higher set discharge electric power level to thereby increase the generation amount of activated species. This therefore makes it possible to generate a streamer discharge at a treatment capability corresponding to the treatment amount of the component to be treated, and the air stream to be treated can be efficiently cleaned and purified.

On the other hand, for example, for the case of an operation in which the air volume of the air blower means (26) is switched to a lower set air volume level, the discharge electric power is set to a lower set discharge electric power level to thereby decrease the generation amount of activated species. This therefore inhibits the treatment capability obtained by streamer discharge from becoming excessive relative to the treatment amount of the component to be treated, thereby preventing the discharge electric power from being wasted.

In addition, the multiple set discharge electric power levels are provided, wherein the discharge electric power is made switchable among the multiple set discharge electric power levels. This makes it possible to more precisely generate an amount of activated species corresponding to the treatment amount of the component to be treated. Accordingly, the air stream to be treated can be more efficiently cleaned and purified and the air purification device can be improved in its energy saving properties.

In accordance with the third invention, the discharge electric power is changed, when the air volume of the air blower means (26) approximates to a set air volume level and when the treatment amount of the component to be treated is stable. This therefore makes it possible to prevent the occurrence of an extra change in the discharge electric power when the air blower means (26) does not yet reach a rated operation. Consequently, it becomes possible to establish an optimum change in the discharge electric power depending on the treatment amount of the component to be treated. This therefore effectively inhibits the discharge electric power from being wasted due to generating a streamer discharge that is excessive relative to the treatment amount of the component to be treated.

In accordance with the fourth invention, the concentration detection means (70) is provided wherein the discharge electric power is increased or decreased depending on the variation in the concentration of the component to be treated detected by the concentration detection means (70). And when the concentration of odorous and harmful components in the indoor space increases, the discharge electric power is increased by a predetermined amount to thereby increase the generation amount of activated species. This therefore makes it possible to generate a streamer discharge at a treatment capability corresponding to the treatment amount of the component to be treated, and the air stream to be treated can be efficiently cleaned and purified.

On the other hand, when the concentration of odorous and harmful components in the indoor space decreases, the discharge electric power is decreased by a predetermined amount to thereby decrease the generation amount of activated species. This therefore inhibits the treatment capability obtained by streamer discharge from becoming excessive relative to the treatment amount of the component to be treated, thereby preventing the discharge electric power from being wasted. Consequently, the air purification device is improved in its energy saving properties.

In addition, in accordance with this invention, it is arranged such that the discharge electric power of the discharge device (40) is made to change based on the concentration detected by the concentration detection means (70), which arrangement makes it possible to automatically make changes in the discharge electric power depending on the concentration of the component to be treated.

In accordance with the fifth invention, the concentration detection means (70) is provided wherein based on the variation in the concentration of the component to be treated that is detected by the concentration detection means (70) the air volume of the air blower means (26) is increased or decreased and, in addition, the discharge electric power is increased or decreased. Consequently, for example, when the concentration of the component to be treated in the indoor space is high, the air volume of the air blower means (26) is increased to thereby accelerated the rate at which the component to be treated is treated, whereby the indoor space is rapidly cleaned and purified. In addition, at this time, it becomes possible to generate an amount of activated species corresponding to the treatment amount of the component to be treated by increasing the discharge electric power depending on the concentration of the component to be treated, whereby the air stream to be treated is efficiently cleaned and purified.

On the other hand, for example, when the concentration of odorous and harmful components in the indoor space is low, the air volume of the air blower means (26) is decreased, thereby making it possible to inhibit the air blower means (26) from being operated excessively. Accordingly, the operation power of the air blower means (26) can be cut down. In addition, at this time, it becomes possible to generate an amount of activated species corresponding to the treatment amount of the component to be treated by decreasing the discharge electric power depending on the concentration of the component to be treated. This therefore inhibits the treatment capability obtained by streamer discharge from becoming excessive relative to the treatment amount of the component to be treated, thereby preventing the discharge electric power from being wasted.

In addition, in accordance with this invention, it is arranged such that based on the concentration detected by the concentration detection means (70) the air volume of the air blower means (26) and the discharge electric power of the discharge device (40) are each switched among the set levels. This arrangement makes it possible to allow the air purification device to perform automatic operations depending on the concentration of the component to be treated.

BRIEF DESCRIPTION OF THE DRAWINGS

FIG. 5 is a table which represents an operation condition example of the air purification device of the first embodiment;

FIG. 7 is a table which represents an operation condition example of the air purification device of the first variation;

FIG. 8 is a table which represents an operation condition example of an air purification device according to a second variation of the first embodiment;

FIG. 11 is a table which represents an operation condition example of the air purification device of the third embodiment;

REFERENCE NUMERALS IN DRAWINGS

Figure 1:
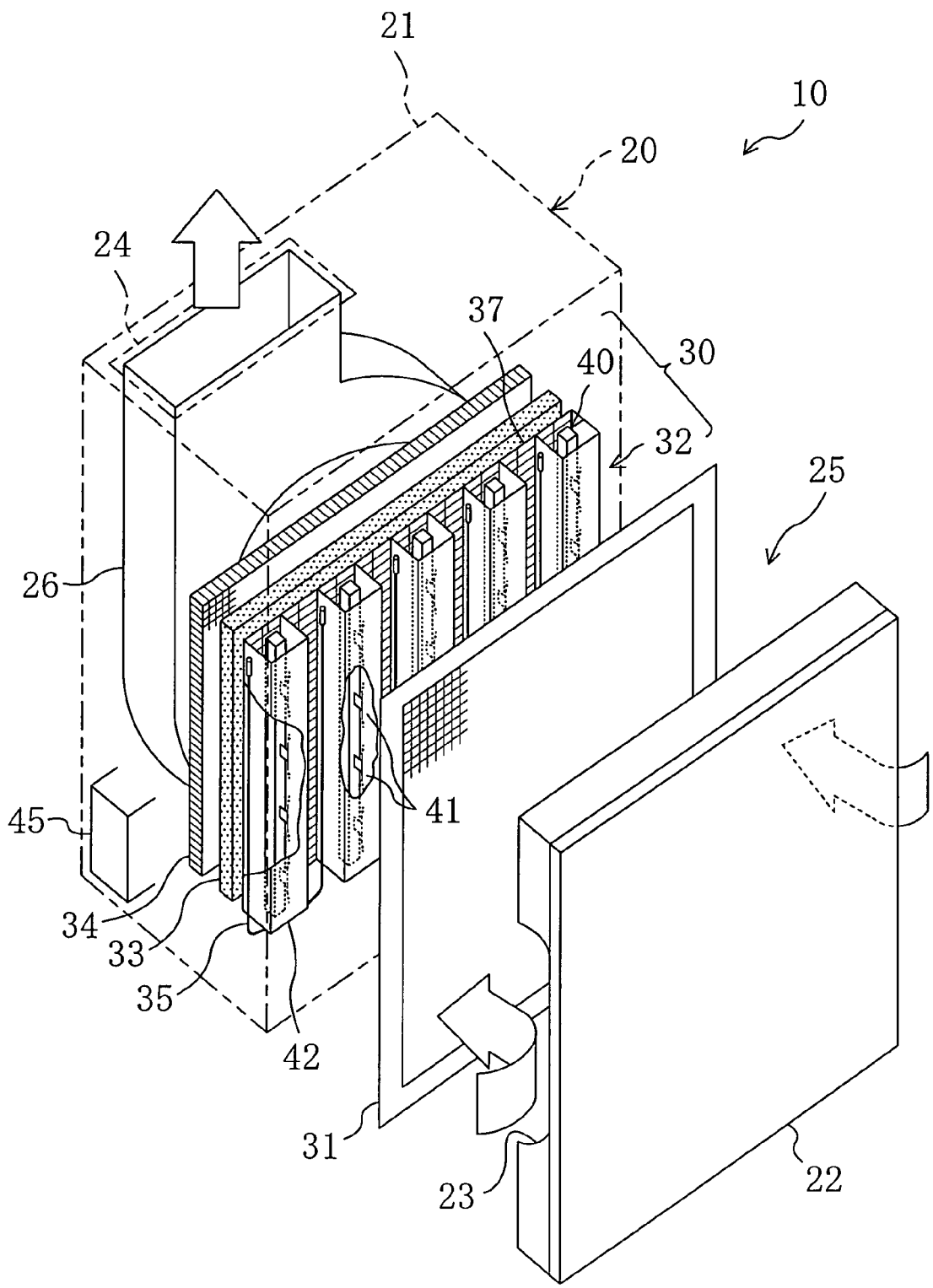
FIG. 1 is a schematic perspective view which illustrates the overall construction of an air purification device according to a first embodiment of the present invention.

(10) air purification device
(26) air blower means
(40) discharge device (40a, 40b)
(41) discharge electrode
(42) counter electrode
(45) electric power supply means
(63) discharge control part
(64) air volume control part
(65) high voltage electric power supply (71, 72)
(70) concentration detection means

BEST MODE FOR CARRYING OUT THE INVENTION

Preferred embodiments of the present invention are described in detail with reference to the drawing figures.

First Embodiment of the Invention

Referring first to FIGS. 1 through 4, an air purification device (10) according to a first embodiment of the present invention is described.

Figure 2:
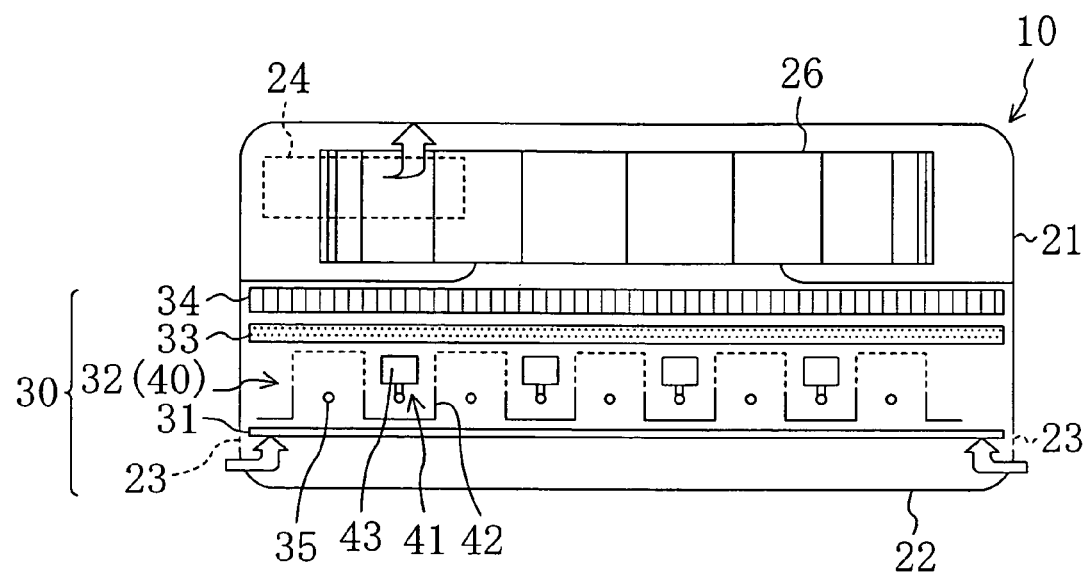
FIG. 2 is a constructional diagram which illustrates the inside of a discharge device of the first embodiment when viewed from above.

FIG. 1 is a perspective view which illustrates in exploded manner the air purification device (10) of the first embodiment. FIG. 2 is a diagram which depicts the inside of the air purification device (10) when viewed from above. This air purification device (10) is a consumer air purification device intended for use in general household, small stores et cetera. In addition, the air purification device (10) is a so-called streamer discharge type air purification device which produces a low temperature plasma by generation of a streamer discharge to thereby purify a stream of air to be treated.

The air purification device (10) includes a casing (20). The casing (20) is made up of a box-like casing main body (21) with an open end surface and a front plate (22) which is placed on the open end surface. An air suction opening (23) is formed in each side surface of the casing (20) on the side of the front plate (22). In addition, an air blowout opening (24) is formed in the top plate of the casing main body (21). More specifically, the air blowout opening (24) is located adjacent to the rear plate of the casing main body (21).

An air passageway (25) is formed within the casing (20). The air passageway (25) extends from the air suction opening (23) to the air blowout opening (24). Room air which is a stream of air to be treated is made to flow through the air passageway (25). A functional section (30) including various air purification components, and a centrifugal air blower (air blower means) (26) configured to cause room air to be distributed through the air passageway (25) are disposed in the air passageway (25) in that order in the direction from the upstream side (the bottomside in FIG. 2) to the downstream side of the flow of the room air.

Disposed, in sequence from the side of the front plate (22), in the functional section (30) are a pre-filter (31), an ionization part (32), an electrostatic filter (33), and a catalytic filter (34). A discharge device (40) for low temperature plasma generation is integrally incorporated into the ionization part (32). In addition, an electric power supply means (45) for the discharge device (40) is provided in the casing main body (21) of the air purification device (10). More specifically, the electric power supply means (45) is located adjacent to the rear bottomside of the casing main body (21).

The pre-filter (31) is formed by a filter adapted to entrap and collect dust of relatively large size contained in the air. The ionization part (32) causes dust of relatively small size passing through the pre-filter (31) to be charged electrically. The electrically charged dust is entrapped and collected by the electrostatic filter (33) disposed downstream of the ionization part (32). The ionization part (32) is made up of a plurality of ionization lines (35) and a plurality of counter electrodes (42). The plurality of ionization lines (35) extend between the top end and the bottom end of the ionization part (32) at even intervals. Each ionization line (35) lies on a single virtual surface in parallel with the electrostatic filter (33). The counter electrode (42) is formed by an elongated member having a U-shaped cross section, and its open part is located on the rear side. Each counter electrode (42) is arranged between ionization lines (35), such that it is positioned parallel to the ionization lines (35). And, each counter electrode (42) is joined, at its open part, to a single mesh plate (37).

The discharge device (40) is equipped with a plurality of discharge electrodes (41) and a counter electrode (42) facing the discharge electrodes (41). This counter electrode (42) is shared as the counter electrode (42) of the ionization part (32), and the discharge electrodes (41) are positioned in the inside of the associated counter electrode (42) facing the discharge electrodes (41).

Figure 3:
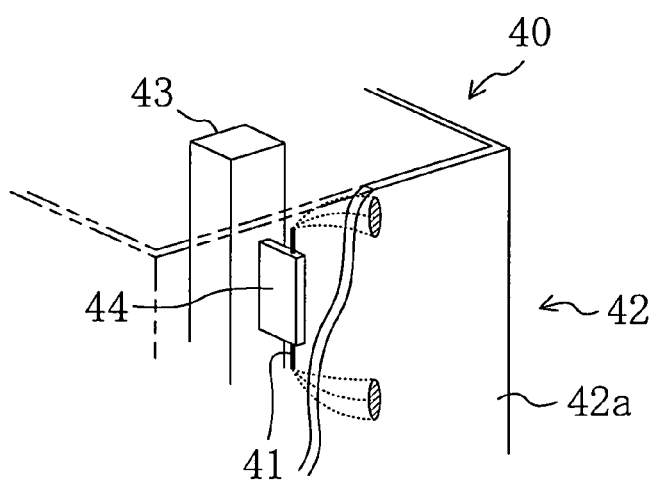
FIG. 3 is a perspective view which illustrates in enlarged manner a main section of the discharge device of the first embodiment.

More specifically, with reference to FIG. 3 which is an enlarged perspective view of the discharge device (40), an electrode holding member (43) extending vertically is provided in the inside of the counter electrode (42). The discharge electrode (41) is held by a fixing member (44) to the electrode holding member (43). The discharge electrode (41) is a linear or rod-like electrode. The discharge electrode (41) projecting outwardly from the fixing member (44) is arranged, such that it runs substantially parallel with a first surface (42a) of the counter electrode (42).

The catalytic filter (34) is disposed downstream of the electrostatic filter (33). The catalytic filter (34) is formed by, for example, a honeycomb structure substrate which supports on its surface a catalyst. As the catalyst, catalysts (such as catalysts of the manganese family and catalysts of the precious metal family) may be used. These catalysts are capable of further activating high-reactivity substances present in a low temperature plasma generated by electric discharge and capable of promoting the decomposition of harmful components and odorous components in the air. In addition, the catalytic filter (34) supports thereon activated charcoal and exhibits capability of adsorbing a component to be treated that is contained in a stream of air to be treated.

Next, the configuration of the electric power supply means (45) which is a feature of the present invention is described with reference to the block diagram of FIG. 4. The electric power supply means (45) includes an operation input signal detection part (61) for detecting an operation signal which is issued by operating, for example, a remote controller or control panel, and an equipment operation control part (62) capable of receiving a detection signal from the operation input signal detection part (61). The electric power supply means (45) further includes a discharge control part (63) and an air volume control part (64) both of which are controlled by the equipment operation control part (62), and a high voltage electric power supply part (65) which outputs predetermined electric power (electric current) to the discharge device (40) within the device main body.

The air volume control part (64) is configured such that it outputs a control signal to the centrifugal air blower (26) which is an air blower means to thereby cause the air volume of the centrifugal air blower (26) to switch among a plurality of set air volume levels. More specifically, the centrifugal air blower (26) of the present embodiment is so configured as to be able to operate among first to five set air volume levels (i.e. from Operation A to Operation E of FIG. 5).

The discharge control part (63) is made up of an electric current control part (63a) and an ON/OFF control part (63b). The electric current control part (63a) is configured such that it outputs a signal for electric current control to an electric current value set part (65a) of the high voltage electric power supply part (65), whereby electric power (electric current), supplied to the discharge device (40) from the high voltage electric power supply part (65), becomes changeable. The ON/OFF control part (63b) outputs an ON/OFF switch signal to the high voltage electric power supply part (65) to thereby make the high voltage electric power supply part (65) switchable between the ON state and the OFF state.

The electric current control part (63a) of the discharge control part (63) in the above-described electric power supply means (45) is configured such that it increases or decreases the discharge electric power of the discharge device (40) depending on the air volume of the centrifugal air blower (26). More specifically, a first and a second set discharge electric power level are set to the electric current control part (63a). More specifically, the electric current control part (63a) is configured as follows. That is, when the air volume of the centrifugal air blower (26) is at the set air volume level of Operation A, Operation B, or Operation C (see FIG. 5), the discharge electric power of the discharge device (40) is set at the first set discharge electric power level (the discharge electric power whose discharge electric current becomes 37 μA). On the other hand, when the air volume of the centrifugal air blower (26) is at the set air volume of Operation D or Operation E, the discharge electric power of the discharge device (40) is set at the second set discharge electric power level (the discharge electric power whose discharge electric current becomes 5.5 μA) which is lower than the first set discharge electric power level.

In addition, the electric current control part (63a) is configured such that it changes the discharge electric power of the discharge device (40) depending on the air volume of the centrifugal air blower (26) after a set time (t) has elapsed since the air volume control part (64) issued to the centrifugal air blower (26) a signal for the change in air volume level. Here, the time, from when the operation of the centrifugal air blower (26) is made to change to when the air volume of the centrifugal air blower (26) reaches a set air volume level, i.e. when the centrifugal air blower (26) is regarded as having reached its rated operation, is set as the set time (t).

Running Operation

In the following, the basic running operation of the air purification device (10) is described.

As shown in FIG. 1 and FIG. 2, when the air purification device (10) is in operation, the centrifugal air blower (26) is activated at a predetermined set air volume level whereby room air flows through the air passageway (25) in the casing (20). In addition, the high voltage electric power supply part (65) of the electric power supply means (45) (FIG. 4) is turned on and in the discharge device (40) a streamer discharge is generated.

When a stream of room air is introduced into the casing (20), dust of relatively large size is first removed by the pre-filter (31). The room air passes through the ionization part (32), during which passage dust of relatively small size in the room air is electrically charged, and flows downstream, and the dust thus electrically charged is entrapped and collected by the electrostatic filter (33). As described above, airborne dust particles of from large size to small size are almost removed by the pre-filter (31) and by the electrostatic filter (33).

In the discharge device (40) integrally incorporated into the ionization part (32), a low temperature plasma is generated from the tip of the discharge electrode (41) towards the counter electrode (42) (FIG. 3) and, as a result, activated species of high reactivity, such as electron, ion, ozone, and radical et cetera, are produced. When these activated species arrive at the catalytic filter (34), they become further activated, thereby decomposing and removing harmful components and odorous components in the air. And, a stream of cleaned room air, free from dust as well as from harmful and odorous components, is blown out into the room through the air blowout opening (24).

CONTROL EXAMPLE

Figure 4:
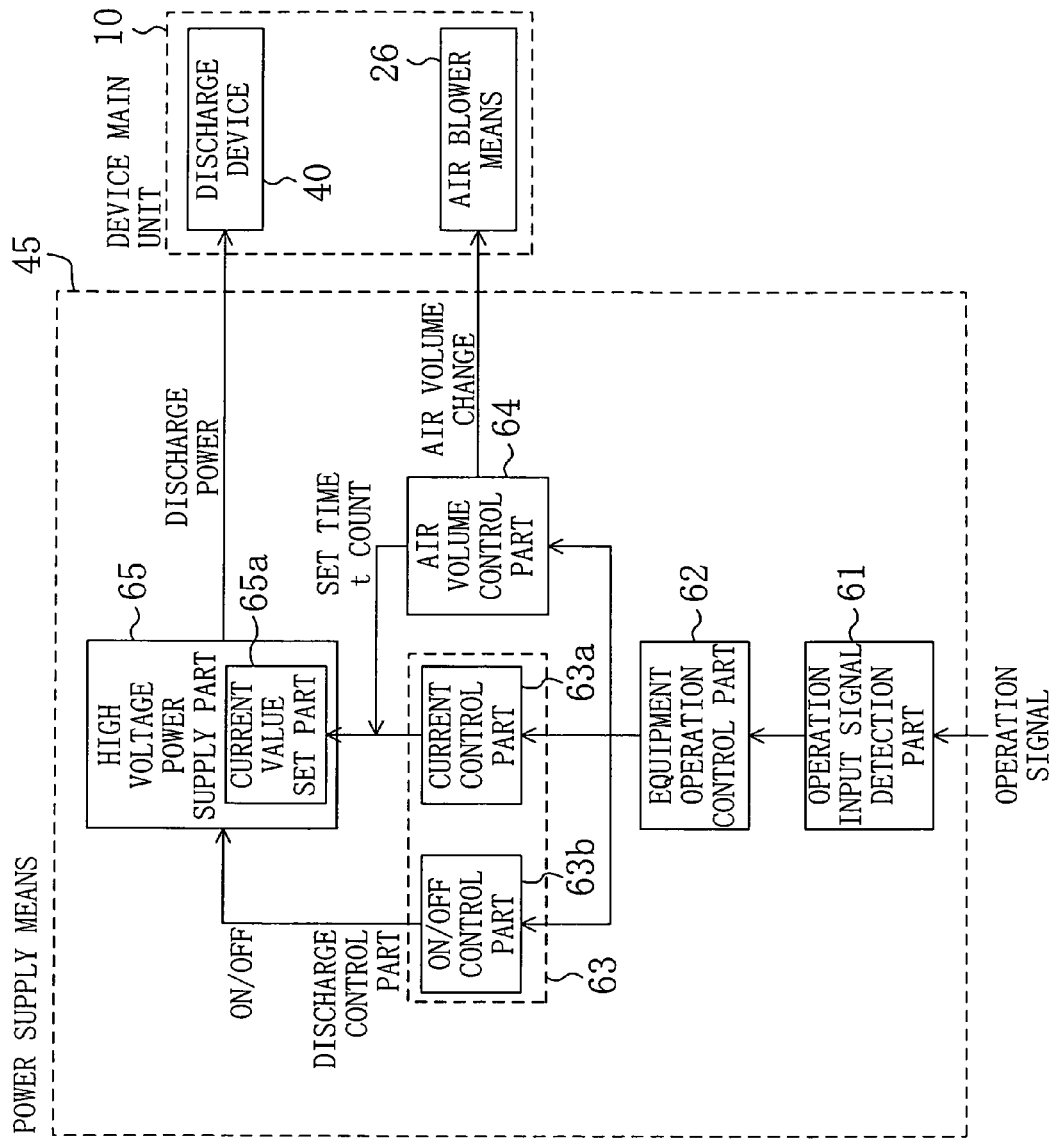
FIG. 4 is a block diagram of the air purification device of the first embodiment.

Next, a specific example of how the air purification device (10) is controlled is described by making reference to FIG. 4 and FIG. 5.

For example, when the concentration of odorous and harmful components in an indoor space in which the air purification device (10) is installed increases, the user operates a remote controller (not shown) so that the remote controller outputs to the operation input signal detection part (61) an operation signal for causing Operation A of FIG. 5 to start.

Then, based on the signal detected by the operation input signal detection part (61), the equipment operation control part (62) outputs a control signal to the discharge control part (63) and the air volume control part (64).

Upon receiving the signal from the equipment operation control part (62), the air volume control part (64) outputs to the centrifugal air blower (26) a control signal so that the centrifugal air blower (26) supplies a current of air at a set air volume level of 6.0 m$^3$/min. Then, the centrifugal air blower (26) performs a rated operation in which air is supplied at a set air volume level of 6.0 m$^3$/min.

In addition, the electric current control part (63a) of the discharge control part (63) which has received the signal from the equipment operation control part (62) outputs to the electric current value set part (65a) of the high voltage electric power supply part (65) an electric current control signal depending on the aforesaid set air volume level. More specifically, the electric current control part (63a) outputs to the electric current value set part (65a) a control signal so that the discharge electric current in the discharge device (40) becomes 37 μA and the discharge electric power at the time of streamer discharge becomes the first set discharge electric power level. In this case, the electric current control signal is fed to the electric current value set part (65a) after the set time (t) has elapsed since the air volume control part (64) issued a control signal to the centrifugal air blower (26). And, when the high voltage electric power supply (65) provides electric power to the discharge device (40), a streamer discharge is generated at the first set discharge electric power level in the discharge device (40). Accordingly, as the treatment amount of the component to be treated increases, the amount of low temperature plasma generated at the time of streamer discharge, i.e., the amount of activated species, increases. This makes it possible to efficiently decompose the component to be treated.

When the concentration of odorous and harmful components in the indoor space is reduced by Operation A, the user operates, for example, the remote controller, to output to the operation input signal detection part (61) an operation signal for causing Operation E of FIG. 5 to start. Then, based on the signal detected by the operation input signal detection part (61), the equipment operation control part (62) outputs a control signal to the discharge control part (63) and the air volume control part (64).

Upon receipt of the signal from the equipment operation control part (62), the air volume control part (64) outputs to the centrifugal air blower (26) a control signal for causing the centrifugal air blower (26) to supply a stream of air at a set air volume level of 0.9 m$^3$/min. Then, the centrifugal air blower (26) performs a rated operation at a set air volume level of 0.9 m$^3$/min.

In addition, the electric current control part (63a) of the discharge control part (63) which has received the signal from the equipment operation control part (62) outputs to the electric current value set part (65a) of the high voltage electric power supply part (65) an electric current control signal depending on the aforesaid set air volume level. More specifically, the electric current control part (63a) outputs to the electric current value set part (65a) a control signal so that the discharge electric current of the discharge device (40) becomes 5.5 μA and the discharge electric power at the time of streamer discharge becomes the second set discharge electric power level. In this case, the electric current control signal is fed to the electric current value set part (65a) after the set time (t) has elapsed since the air volume control part (64) issued a control signal to the centrifugal air blower (26). Then, when electric power is provided to the discharge device (40)

from the high voltage electric power supply part (65), the discharge device (40) generates a streamer discharge at the second set discharge electric power level. Accordingly, as the treatment amount of the component to be treated decreases, the generation amount of activated species at the time of streamer discharge decreases. This makes it possible to efficiently decompose the component to be treated without excessive streamer discharge.

Effects of the First Embodiment

The air purification device of the first embodiment provides the following advantageous effects.

In accordance with the first embodiment, during Operations A, B, and C in which the air volume of the centrifugal air blower (26) is set at high level, the discharge electric power is set at the first discharge electric power level so that the generation amount of activated species by streamer discharge increases. Because of this, even during an operation in which the treatment amount of the component to be treated is relatively large, it becomes possible to provide a treatment capability corresponding to the treatment amount of the component to be treated.

On the other hand, during Operations D and E in which the air volume of the centrifugal air blower (26) is set at low level, the discharge electric power is set at the second discharge electric power level so that the generation amount of activated species by streamer discharge decreases. Because of this, even during an operation in which the treatment amount of the component to be treated is relatively small, it becomes possible to inhibit the treatment capability from becoming excessive relative to the treatment amount of the component to be treated. Accordingly, it becomes possible for the air purification device to provide a treatment capability corresponding to the treatment amount of the component to be treated. Accordingly, the air purification device can be improved in its energy saving properties.

In addition, in accordance with the first embodiment, the discharge electric power is designed to increase on the condition that the air volume of the centrifugal air blower (26) is set at high level at which the operating sound of the centrifugal air blower (26) is relatively high. This therefore makes it possible to mask discharge sounds generated at the time of streamer discharge by the operating sound of the centrifugal air blower (26), thereby inhibiting the discharge sounds at the time of streamer discharge from causing discomfort to the user.

On the other hand, the discharge electric power is designed to decrease on the condition that the air volume of the centrifugal air blower (26) is set at low level at which the operating sound of the centrifugal air blower (26) is relatively low. As a result, even when the operating sound of the centrifugal air blower (26) is low, it becomes possible to make the user harder to hear discharge sounds generated at the time of streamer discharge. This therefore makes it possible to improve the comfort of the space where the air purification device is installed.

Furthermore, in accordance with the first embodiment, a streamer discharge is generated at a corresponding treatment capability to the treatment amount of the component to be treated. This makes it possible to inhibit the generation of activated species (such as ozone) from becoming excessive relative to the treatment amount of the component to be treated, whereby the emission of unreacted ozone with the component to be treated to outside the device is effectively prevented. Consequently, the air purification device can be improved in its reliability.

In addition to the above, in accordance with the first embodiment, the discharge electric power is made to change after elapse of the set time (t) at which the centrifugal air blower (26) is regarded as having reached its rated operation. Because of this, the discharge electric power can be made to change with the air volume of the centrifugal air blower (26) being in a stable state. Accordingly, the discharge electric power can be optimally made to change depending on the treatment amount of the component to be treated, and the air stream to be treated can be efficiently cleaned and purified.

First Variation of the First Embodiment

Figure 6:
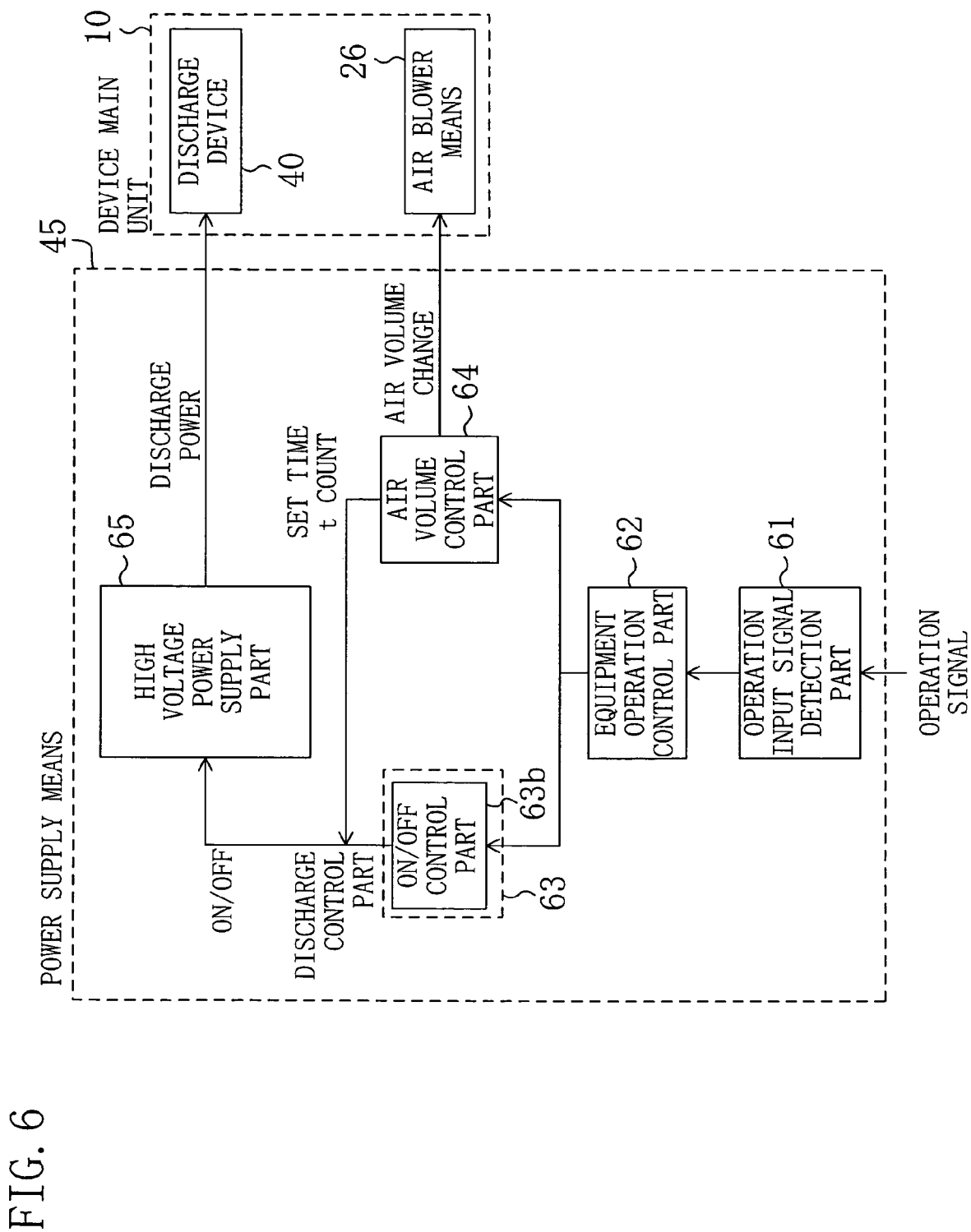
FIG. 6 is a block diagram of an air purification device according to a first variation of the first embodiment.

Referring next to FIG. 6 and FIG. 7, a first variation of the air purification device (10) of the first embodiment is described below. The air purification device (10) of the first variation differs in configuration of the electric power supply means (45) from the first embodiment. More specifically, the discharge control part (63) of the electric power supply means (45) is made up of the ON/OFF control part (63b) alone, and the high voltage electric power supply part (65) does not include the aforesaid electric current value set part. And the ON/OFF control part (63b) of the discharge control part (63) is so configured as to change the discharge electric power of the discharge device (40) depending on the air volume of the centrifugal air blower (26). More specifically, the centrifugal air blower (26) is configured such that it turns on the discharge electric power of the discharge device (40) when the air volume of the centrifugal air blower (26) is at the set air volume level of Operation A, Operation B, or Operation C (see FIG. 7), whereby the discharge electric power is at the first set discharge electric power level (i.e. the discharge electric power whose discharge electric current becomes 37 µA), while on the other hand the electric current control part (63a) is configured such that it turns off the discharge electric power of the discharge device (40) (the second set discharge electric power level) when the air volume of the centrifugal air blower (26) is at the set air volume level of Operation D or Operation E (FIG. 7).

With the above configuration, when the concentration of odorous and harmful components in the indoor space becomes high, the user operates for example the remote controller to output to the operation input signal detection part (61) an input signal for causing Operation A of FIG. 7 to start. Then, based on the signal detected by the operation input signal detection part (61), the equipment operation control part (62) outputs a control signal to the discharge control part (63) and the air volume control part (64).

Upon receipt of the signal from the equipment operation control part (62), the air volume control part (64) outputs to the centrifugal air blower (26) a control signal for causing the centrifugal air blower (26) to supply a current of air at a set air volume level of 6.0 m³/min. And the centrifugal air blower (26) performs a rated operation at a set air volume level of 6.0 m³/min.

In addition, the ON/OFF control part (63b) of the discharge control part (63) which has received the signal from the equipment operation control part (62) outputs a signal for causing the high voltage electric power part (65) to switch on depending on the air volume of the centrifugal air blower (26). This signal is received by the high voltage electric power supply part (65) after the aforesaid set time (t) has elapsed since the air volume control part (64) issued a control signal to the centrifugal air blower (26). Upon receipt of this signal, the high voltage electric power supply part (65) enters the ON state and outputs to the discharge device (40) such electric power that the discharge electric current in the discharge device (40) becomes 37 µA. And in the discharge device (40), a streamer discharge is generated at the first set discharge electric power level. Accordingly, as the treatment amount of the component to be treated increases, the generation amount of activated species at the time of streamer discharge increases, and the component to be treated is efficiently decomposed.

When the odorous and harmful components in the indoor space are almost cleaned and purified by Operation A, the user operates, for example, the remote controller, to output to the operation input signal detection part (61) an operation signal for causing Operation E of FIG. 7 to start. As a result of this, based on the signal detected by the operation input signal detection part (61), the equipment operation control part (62) outputs a control signal to the discharge control part (63) and the air volume control part (64). Upon receipt of the signal from the equipment operation control part (62), the air volume control part (64) outputs to the centrifugal air blower (26) a control signal for causing the centrifugal air blower (26) to supply a current of air at a set air volume level of 0.9 m$^3$/min. And the centrifugal air blower (26) performs a rated operation at 0.9 m$^3$/min.

Meanwhile, the ON/OFF control part (63b) of the discharge control part (63) which has received the signal from the equipment operation control part (62) outputs a signal for causing the high voltage electric power supply part (65) to switch off depending on the air volume of the centrifugal air blower (26). This signal is received by the high voltage electric power supply part (65) after the aforesaid set time (t) has elapsed since the air volume control part (64) issued a control signal to the centrifugal air blower (26). Upon receipt of this signal, the high voltage electric power supply part (65) enters the OFF state and no electric power is supplied to the discharge device (40). Accordingly, in the discharge device (40), no streamer discharge is generated, and the component to be treated is not decomposed by streamer discharge.

In the air purification device (10) of the first variation, the discharge electric power of the discharge device (40) is turned off when the concentration of odorous and harmful components in the indoor space is at extremely low levels. This makes it possible to perform an operation that stresses energy savings. During such an energy saving operation, the component to be treated is decomposed and removed by the adsorptive decomposition action of the foregoing catalytic filter (34).

Besides, in the first variation, during Operation D or Operation E in which the operating sound of the centrifugal air blower (26) is low, no streamer discharge is generated. Accordingly, in situations that require quiet operation of the device, for example, in an office space at the meeting time and in a living space at the nighttime, discharge sounds generated by streamer discharge are surely inhibited. This makes it possible to effectively reduce noise emission from the air purification device (10).

Second Variation of the First Embodiment

Referring next to FIG. 4 and FIG. 8, a second variation of the air purification device (10) of the first embodiment is described below. The air purification device (10) of the second variation differs from the first embodiment in that the electric power supply means (45) is controlled in a different way. More specifically, five different set discharge electric power levels (first to fifth set discharge electric power levels) respectively corresponding to the set air volume levels of the centrifugal air blower (26) are set for the electric current control part (63a) of the discharge control part (63) of the second variation, as shown in FIG. 8.

In the air purification device (10) of the second variation, for example, when the concentration of odorous and harmful components in the indoor space becomes considerably high and the user operates the remote controller to output a signal for causing Operation A to start, the air volume of the centrifugal air blower (26) becomes a set air volume level of 6.0 m$^3$/min in Operation A of FIG. 8. In response to this, the electric current control part (63a) outputs a signal to the electric current value set part (65a) so that in the discharge device (40) a streamer discharge is generated by a discharge electric current of 37 µA (the first set discharge electric power level). Accordingly, the discharge electric power of the discharge device (40) is maximized and, as a result, the generation amount of activated species at the time of streamer discharge is increased to a maximum.

On the other hand, for example, when the concentration of odorous and harmful components in the indoor space becomes considerably low and the user operates the remote controller to output a signal for causing Operation E to start, the air volume of the centrifugal air blower (26) becomes a set air volume level of 0.9 m$^3$/min in Operation E of FIG. 8. In response to this, the electric current control part (63a) outputs a signal to the electric current value set part (65a) so that in the discharge device (40) a streamer discharge is generated by a discharge electric current of 5.5 µA (the fifth set discharge electric power level). Accordingly, the discharge electric power of the discharge device (40) is minimized and, as a result, the generation amount of activated species at the time of streamer discharge is decreased to a minimum.

Furthermore, for example, when the concentration of odorous and harmful components is intermediate between the concentration in Operation A and the concentration in Operation E and the user operates the remote control to output a signal for causing Operation C to start, the air volume of the centrifugal air blower (26) becomes a set air volume level of 2.7 m$^3$/min in Operation C of FIG. 8. In response to this, the electric current control part (63a) outputs a signal to the electric current value set part (65a) so that in the discharge device (40) a streamer discharge is generated by a discharge electric current of 20 µA (the third set discharge electric power level). Accordingly, the discharge electric power of the discharge device (40) becomes approximately intermediate between the discharge electric power in Operation A and the discharge electric power in Operation E, and the generation amount of activated species at the time of streamer discharge becomes approximately intermediate between the activated species generation amount in Operation A and the activated species generation amount in Operation E.

In the way as described above, in the second variation, the discharge electric power of the streamer discharge is multi stage-controlled depending on the set air volume level of the centrifugal air blower (26). Accordingly, it becomes possible to precisely change the discharge electric power in accordance with the treatment amount of the component to be treated, and the air stream to be treated can be cleaned and purified at high energy efficiency.

Second Embodiment

In the following, an air purification device (10) according to a second embodiment of the present invention is described with reference to FIG. 9. The air purification device (10) of the second embodiment differs in configuration of the electric power supply means (45) from the first embodiment, but the other configurations are the same as the first embodiment. In the following, only the difference from the first embodiment is described.

Figure 9:
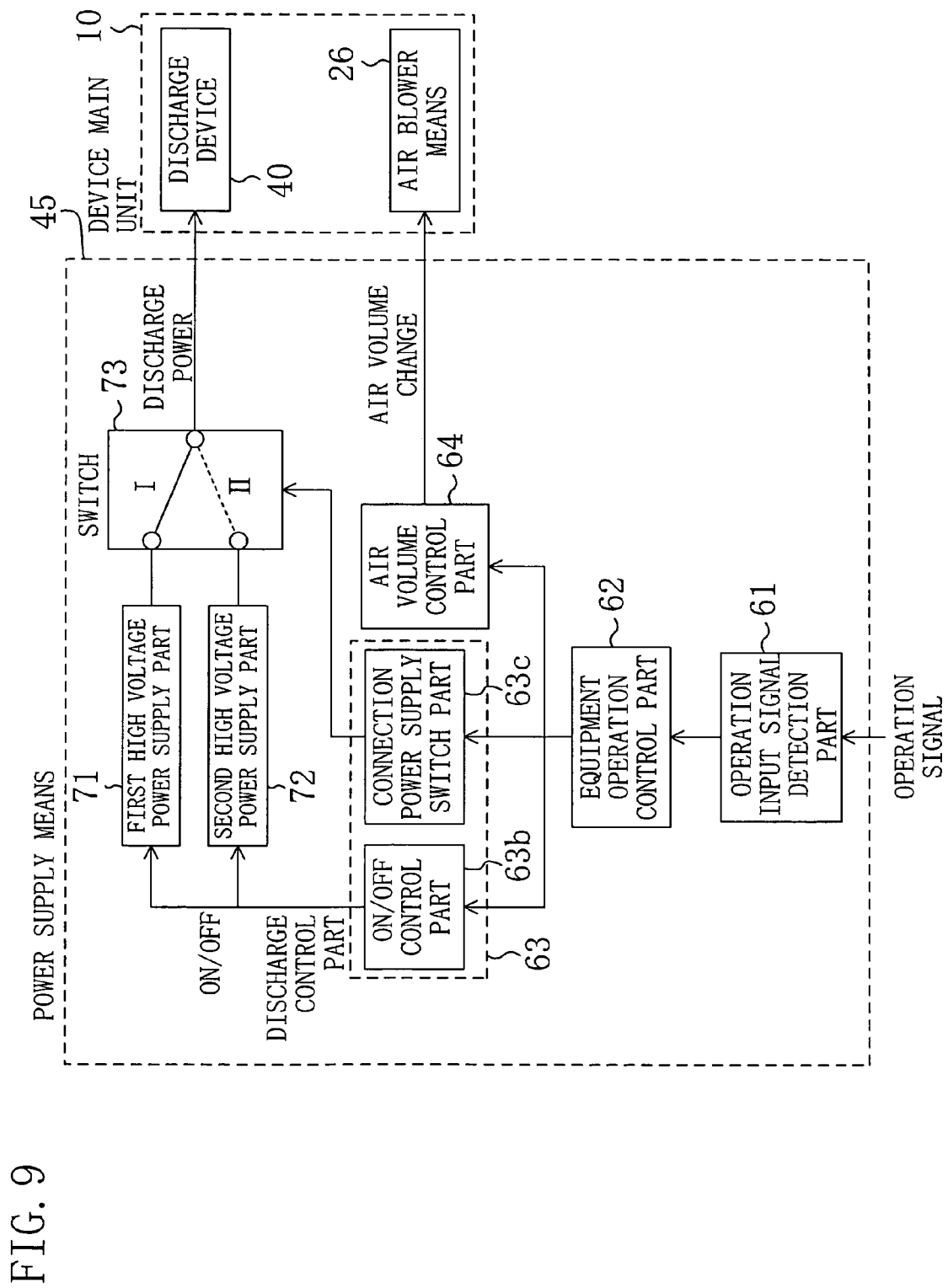
FIG. 9 is a block diagram of an electric power supply means of an air purification device according to a second embodiment of the present invention.

As shown in FIG. 9, the electric power supply means (45) of the second embodiment includes two high voltage electric power supply parts, namely a first high voltage electric power supply part (71) and a second high voltage electric power supply part (72). These high voltage electric power supply parts (71, 72) have different specifications and are configured such that they output different levels of electric power (electric current) to the discharge device (40). More specifically, the first high voltage electric power supply part (71) is configured to provide such a level of electric power to the discharge device (40) that a streamer discharge is generated by a discharge electric current of 37 μA (the first set discharge electric power level) in the discharge device (40), while on the other hand the second high voltage electric power supply part (72) is configured to provide such a level of electric power to the discharge device (40) that a streamer discharge is generated by a discharge electric current of 5.5 μA (the second set discharge electric power level) in the discharge device (40).

In addition, the electric power supply means (45) is provided with a switch (73) which is capable of switching between a first state (indicated by I of FIG. 9) in which the first electric power supply means (71) and the discharge device (40) are connected together while the second electric power supply means (72) and the discharge device (40) are disconnected from each other, and a second state (indicated by II of FIG. 9) in which the second electric power supply means (72) and the discharge device (40) are connected together while the first electric power supply means (71) and the discharge device (40) are disconnected from each other. The switch (73) is configured so as to be made switchable between the first state and the second state by a connection electric power supply switch part (63c) disposed in the discharge control part (63). The connection electric power supply switch part (63c) is configured such that it is controlled by a signal received from the equipment operation control part (62).

CONTROL EXAMPLE

Referring next to FIG. 5 and FIG. 9, an example of how the air purification device (10) of the second embodiment is controlled is described below.

The user operates a remote controller (not shown) to output to the operation input signal detection part (61) an operation signal for causing Operation A of FIG. 5 to start, when the concentration of odorous and harmful components in the indoor space increases. As a result of this, based on the signal detected by the operation input signal detection part (61), the equipment operation control part (62) outputs a control signal to the discharge control part (63) and the air volume control part (64).

Upon receipt of the signal from the equipment operation control part (62), the air volume control part (64) outputs to the centrifugal air blower (26) a control signal for causing the centrifugal air blower (26) to supply a stream of air at a set air volume level of 6.0 m$^3$/min. Then, the centrifugal air blower (26) performs a rated operation at a set air volume level of 6.0 m$^3$/min.

In addition, the connection electric power supply switch part (63c) of the discharge control part (63) which has received the signal from the equipment operation control part (62) controls the switch (73) to change state to the first state in response to variation in the air volume of the centrifugal air blower (26). In the first state, the first high voltage electric power supply part (71) and the discharge device (40) are connected together, so that in the discharge device (40) a streamer discharge is generated by a discharge electric current of 37 μA, i.e., the first set discharge electric power level. Accordingly, as the treatment amount of the component to be treated increases, the generation amount of activated species at the time of streamer discharge increases. This makes it possible to efficiently decompose the component to be treated.

When the concentration of odorous and harmful components in the indoor space is reduced by Operation A, the user operates, for example, the remote controller, to output to the operation input signal detection part (61) an operation signal for causing Operation E of FIG. 5 to start. As a result of this, based on the signal detected by the operation input signal detection part (61), the equipment operation control part (62) outputs a control signal to the discharge control part (63) and the air volume control part (64).

Upon receipt of the signal from the equipment operation control part (62), the air volume control part (64) outputs to the centrifugal air blower (26) a control signal for causing the centrifugal air blower (26) to supply a stream of air at a set air volume level of 0.9 m$^3$/min. Then, the centrifugal air blower (26) performs a rated operation at a set air volume level of 0.9 m$^3$/min.

In addition, the connection electric power supply switch part (63c) of the discharge control part (63) which has received the signal from the equipment operation control part (62) controls the switch (73) to change state to the second state in response to variation in the air volume of the centrifugal air blower (26). In the second state, the second high voltage electric power supply part (72) and the discharge device (40) are connected together, so that in the discharge device (40) a streamer discharge is generated by a discharge electric current of 5.5 μA, i.e., the second set discharge electric power level. Accordingly, as the treatment amount of the component to be treated decreases, the generation amount of activated species at the time of streamer discharge decreases. This makes it possible to efficiently decompose the component to be treated without excessive streamer discharge.

As described above, although the second embodiment differs in configuration of the electric power supply means (45) from the first embodiment, the former is able to provide the same operation control as the latter. Also in the second embodiment, the air stream to be treated can be efficiently cleaned and purified by generating a streamer discharge at a discharge electric power level depending on the treatment amount of the component to be treated.

Third Embodiment

Figure 10:
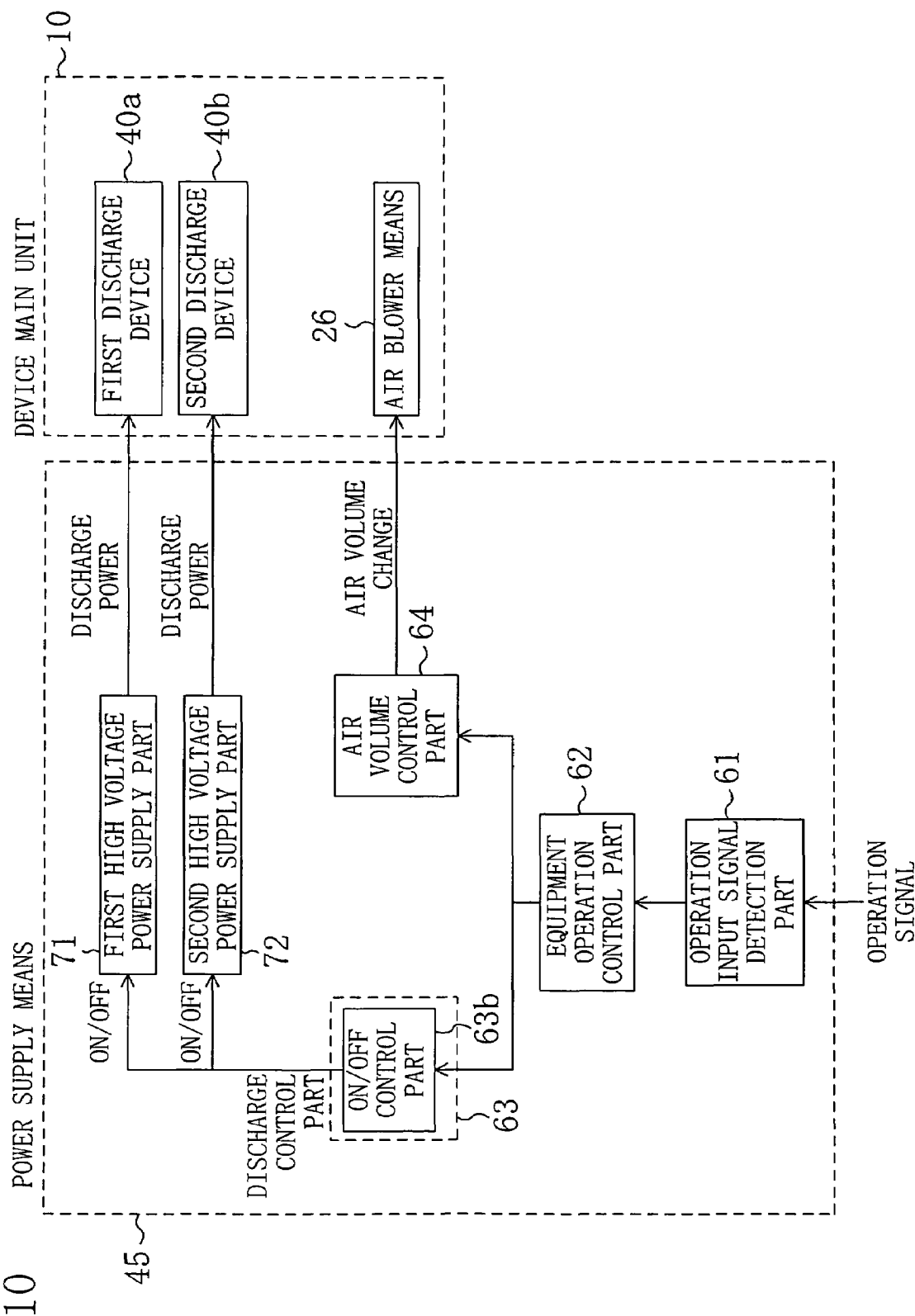
FIG. 10 is a block diagram of an air purification device according to a third embodiment of the present invention.

Referring now to FIG. 10, an air purification device (10) of a third embodiment of the present invention is described below. In the air purification device (10) of the third embodiment, a plural number of discharge electrodes (41) and a counter electrode (42) situated face to face with each discharge electrode (41) are blocked in two discharge devices, i.e. a first discharge device (40a) and a second discharge device (40b). And a first high voltage electric power supply part (40a) associated with the first discharge device (40a) and a second high voltage electric power supply part (40b) associated with the second discharge device (40b) are provided. Note that the first high voltage electric power supply part (40a) and the second high voltage electric power supply part (40b) are identical in their specification with each other, each being configured so as to provide electric power to its associated discharge device in which a streamer discharge is generated by a discharge electric current of 37 μA. In addition, the discharge control part (63) is provided with an ON/OFF control part (63b) which is capable of ON/OFF control of each of the first and second high voltage electric power supply parts (40a, 40b). The other configurations of the air purification device (10) are the same as the first embodiment.

CONTROL EXAMPLE

Referring next to FIG. 10 and FIG. 11, an example of how the air purification device (10) of the third embodiment is controlled is described below.

The user operates the remote controller to output to the operation input signal detection part (61) an operation signal for causing Operation A of FIG. 11 to start, for example, when the concentration of odorous and harmful components in the indoor space increases. As a result of this, based on the signal detected by the operation input signal detection part (61), the equipment operation control part (62) outputs a control signal to the discharge control part (63) and the air volume control part (64).

Upon receipt of the signal from the equipment operation control part (62), the air volume control part (64) outputs to the centrifugal air blower (26) a control signal for causing the centrifugal air blower (26) to supply a current of air at a set air volume level of 6.0 m$^3$/min. Then, the centrifugal air blower (26) performs a rated operation at a set air volume level of 6.0 m$^3$/min.

In addition, the ON/OFF control part (63b) of the discharge control part (63) which has received the signal from the equipment operation control part (62) outputs a signal to both the electric power supply parts (71, 72) so that both the first discharge device (40a) and the second discharge device (40b) turn on in response to variation in the air volume of the centrifugal air blower (26). As a result, in the first discharge device (40a) as well as in the second discharge device (40b), a streamer discharge is generated at a discharge electric current of 37 µA. And the total of the discharge electric power of the first discharge device (40a) and the discharge electric power of the second discharge device (40b) becomes the first set discharge electric power level. Accordingly, as the treatment amount of the component to be treated increases, the generation amount of activated species at the time of streamer discharge increases. This therefore makes it possible to efficiently decompose the component to be treated.

On the other hand, when the concentration of odorous and harmful components in the indoor space is reduced by Operation A, the user operates, for example, the remote controller to output to the operation input signal detection part (61) an operation signal for causing Operation E of FIG. 11 to start. As a result of this, based on the signal detected by the operation input signal detection part (61), the equipment operation control part (62) outputs a control signal to the discharge control part (63) and the air volume control part (64).

Upon receipt of the signal from the equipment operation control part (62), the air volume control part (64) outputs to the centrifugal air blower (26) a control signal for causing the centrifugal air blower (26) to supply a current of air at a set air volume level of 0.9 m$^3$/min. Then, the centrifugal air blower (26) performs a rated operation at a set air volume level of 0.9 m$^3$/min.

In addition, the ON/OFF control part (63b) of the discharge control part (63) which has received the signal from the equipment operation control part (62) outputs a signal to the electric power supply parts (71, 72) so that, for example, the first discharge device (40a) and the second discharge device (40b) turn on and off respectively in response to variation in the air volume of the centrifugal air blower (26). As a result, a streamer discharge is generated at a discharge electric current of 37 µA in the first discharge device (40a), while on the other hand no streamer discharge is generated in the second discharge device (40b). And, the total of the discharge electric power of the first discharge device (40a) and the discharge electric power of the second discharge device (40b) becomes the second set discharge electric power level which is lower than the total discharge electric power level in Operation A (the first set discharge electric power level). As a result, the total generation amount of activated species in the discharge device (40) decreases. Accordingly, since the treatment amount of the component to be treated is decreased, no excessive streamer discharge is generated, and the component to be treated is efficiently decomposed. As described above, in the third embodiment, the overall discharge electric power of the discharge device (40) is reduced by preventing either one of the first and second discharge devices (40a, 40b) of the discharge device (40) from generating a streamer discharge (for example, the second discharge device (40b)). Also in this case, the discharge electric power can be changed in accordance with the treatment amount of the component to be treated, thereby making it possible to effectively clean and purify the air stream to be treated.

In addition, unlike the first embodiment, there is no need to provide the electric current control part (63a) in the third embodiment. Besides, unlike the second embodiment, there is no need to provide the switch (73). Accordingly, the electric power supply means (45) can be simplified in its circuitry.

Fourth Embodiment

Figure 12:
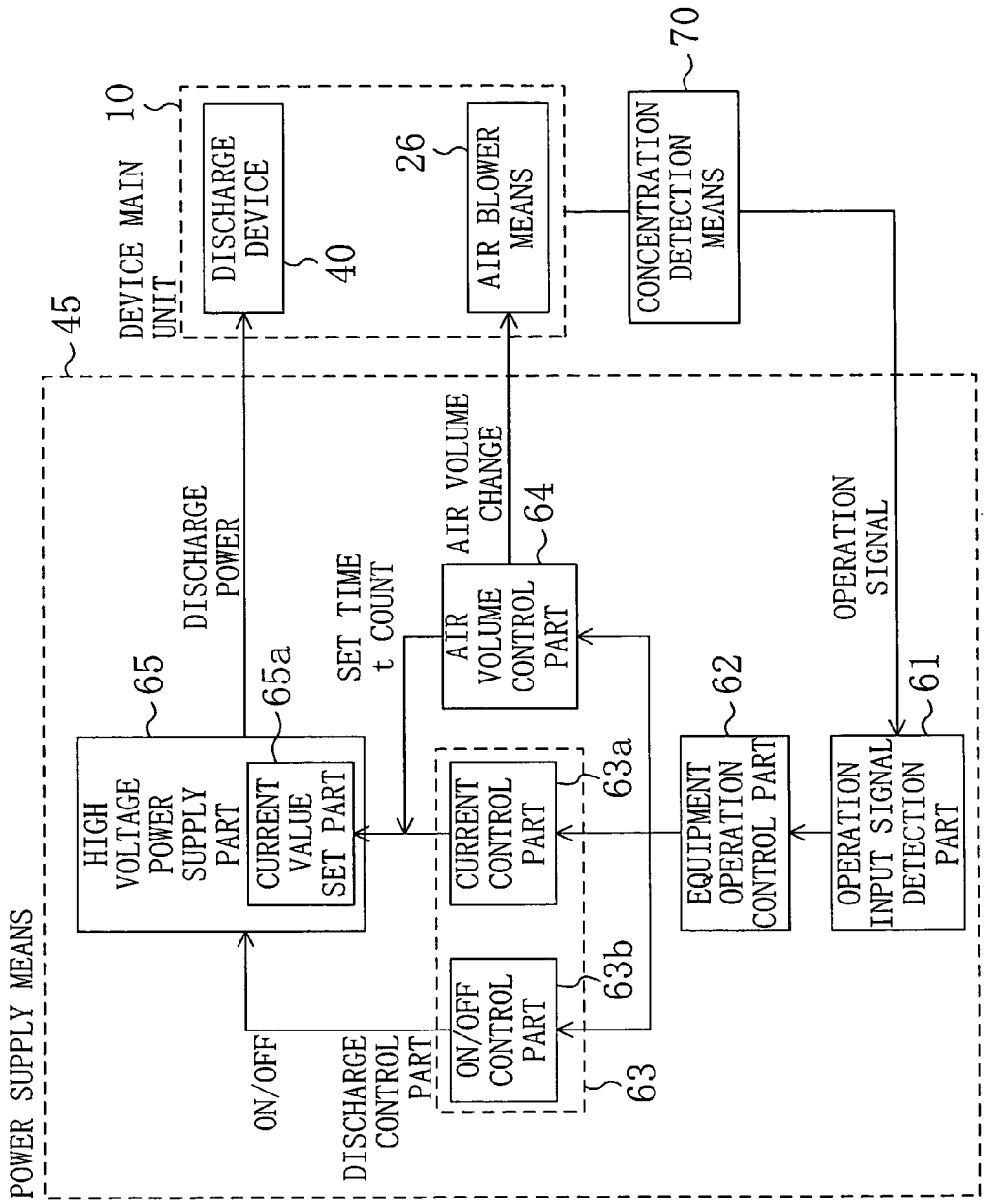
FIG. 12 is a block diagram of an air purification device according to a fourth embodiment of the present invention.
Figure 13:
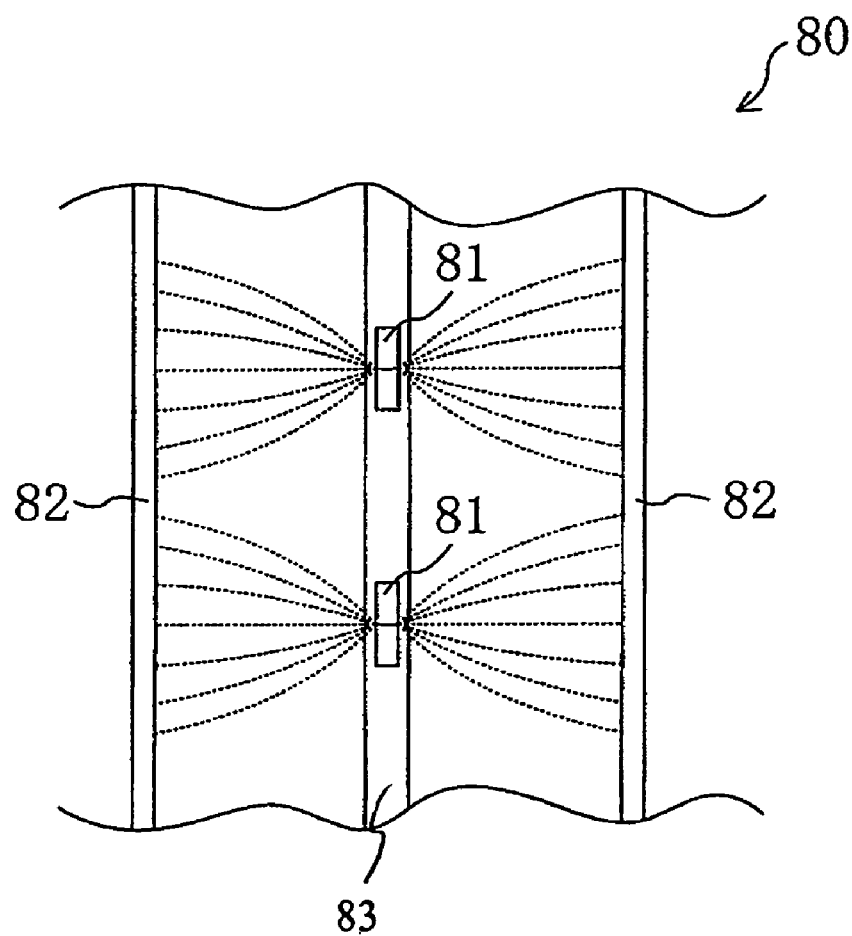
FIG. 13 is an enlarged diagram of a discharge device of an air purification device according to a conventional technique.

Referring next to FIG. 12, an air purification device according to a fourth embodiment of the present invention is described below. The air purification device of the fourth invention is obtained as a result of addition of a concentration detection means (70) for detecting the concentration of odorous and harmful components (the concentration of the component to be treated) in the indoor space, to the air purification device of the first embodiment. And the electric current control part (63a) of the discharge control part (63) is configured such that it increases or decreases the discharge electric power of the discharge device (40) depending on the concentration of the component to be treated detected by the concentration detection means (70). In addition, likewise, the air volume control part (64) is configured such that it increases or decreases the air volume of the air blower means (26) depending on the concentration of the component to be treated detected by the concentration detection means (70).

Control Example

Referring next to FIG. 12, an example of how the air purification device (10) of the fourth embodiment is controlled is described below. In the air purification device of the fourth embodiment, upon detection of the concentration of the component to be treated, the concentration detection means (70) outputs a signal indicative of the detected concentration to the operation input signal detection part (61). Then, based on the signal detected by the operation input signal detection part (61), the equipment operation control part (62) outputs a control signal to the discharge control part (63) and the air volume control part (64).

Here, when the concentration detection means (70) detects that the concentration of odorous and harmful components in the indoor space is high, in other words when the concentration of the component to be treated is high, the air volume control part (64) outputs to the centrifugal air blower (26) a control signal for causing the air volume of the centrifugal air blower (26) to become high (for example, 6.0 m³/min). And the centrifugal air blower (26) operates at an air volume level of 6.0 m³/min. At the same time, the electric current control part (63a) of the discharge control part (63) outputs a control signal to the electric current value set part (65a) of the high voltage electric power supply part (65) so that the discharge electric power of the discharge device (40) becomes high (the discharge electric power whose discharge electric current becomes, for example, 37 µA). And in the discharge device (40), a streamer discharge is generated at a high discharge electric power level.

On the other hand, when the concentration detection means (70) detects that the concentration of odorous and harmful components in the indoor space is low, in other words when the concentration of the component to be treated is low, the air volume control part (64) outputs to the centrifugal air blower (26) a control signal for causing the air volume of the centrifugal air blower (26) to become low (for example, 0.9 m³/min). And the centrifugal air blower (26) operates at an air volume level of 0.9 m³/min. At the same time, the electric current control part (63a) of the discharge control part (63) outputs a control signal to the electric current value set part (65a) of the high voltage electric power supply part (65) so that the discharge electric power of the discharge device (40) becomes low (the discharge electric power whose discharge electric current becomes, for example, 5.5 µA). And in the discharge device (40), a streamer discharge is generated at a low discharge electric power level.

As described above, in the fourth embodiment, the air volume of the centrifugal air blower (26) and the discharge electric power of the discharge device (40) are increased or decreased depending on the concentration of the component to be treated detected by the concentration detection means (70). Accordingly, the amount of activated species corresponding to the amount of the component to be treated which is based on the concentration of odorous and harmful components in the indoor space can be generated by streamer discharge. Therefore, the air stream to be treated can be efficiently cleaned and purified, whereby the air purification device can be improved in its energy saving properties.

In addition, in the fourth embodiment, both the centrifugal air blower (26) and the discharge device (40) are controlled based on the concentration detected by the concentration detection means (70), thereby making it possible to perform an automatic operation treatment depending on the treatment amount of the component to be treated.

Other Embodiments

In regard to the above-described embodiments, the present invention may be configured as follows. [0116] In the above-described embodiments, by increasing or decreasing the discharge electric power after the set time (t) has elapsed since the operation of the centrifugal air blower (26) was switched, the discharge electric power is controlled in accordance with the air volume of the centrifugal air blower (26) in the rated operation. Alternatively, for example, it may be arranged such that the frequency or the electric current value of the centrifugal air blower (26) is first detected to thereby determine whether the centrifugal air blower (26) has substantially reached a preset air volume level and then the discharge power electric is controlled.

In addition, in the above-described embodiments, when the air volume of the centrifugal air blower (26) is switched to a low set air volume level because, for example, the concentration of odorous and harmful components in the indoor space is low, the discharge electric power is reduced after elapse of the set time (t). Alternatively, it may be arranged such that when the air volume of the centrifugal air blower (26) is switched from "a high set air volume level" to "a low set air volume level", the discharge electric power is reduced instantaneously. In this case, discharge sounds generated at the time of streamer discharge are surely prevented from being easily heard to the ears of the user until the time the air volume of the centrifugal air blower (26) reaches "the low set air volume level".

In addition, in the fourth embodiment, both the air volume of the centrifugal air blower (26) and the discharge electric power of the discharge device (40) are increased or decreased depending on the concentration of the component to be treated which is detected by the concentration detection means (70). Alternatively, it may be arranged such that only the discharge electric power of the discharge device (40) is increased or decreased depending on the concentration of the component to be treated which is detected by the concentration detection means (70). In this case, for example, the air volume of the centrifugal air blower (26) is made constant, and by increasing or decreasing the discharge electric power based on the concentration of the component to be treated, it becomes possible to generate, by streamer discharge, a corresponding amount of activated species to the treatment amount of the component to be treated.

INDUSTRIAL APPLICABILITY

The present invention provides an air purification device useful as a consumer air purification device and an air purification device for business use.

What is claimed is:

1. An air purification device comprising:
   a discharge device for generating a streamer discharge between a discharge electrode and a counter electrode facing the discharge electrode;
   an electric power supply for applying voltages to both the electrodes; and
   an air blower for distributing to the discharge device a stream of air to be treated, the air purification device being capable of decomposing, by the streamer discharge, a component to be treated which is contained in the air stream to be treated;
   an air volume control part for switching the air volume of the air blower among a plurality of set air volume levels; and
   a discharge control part configured to switch the discharge electric power of the discharge device to one of a plurality of set discharge electric power levels depending on the air volume level set in the air blower.

2. The air purification device of claim 1, wherein:
   the discharge control part is configured so that the discharge electric power is made to change after a set time (t) has elapsed since the air volume of the air blower means was made to change by the air volume control part.

3. An air purification device comprising:
   a discharge device for generating a streamer discharge between a discharge electrode and a counter electrode facing the discharge electrode;
   an electric power supply for applying voltages to both the electrodes; and an air blower for distributing to the discharge device a stream of air to be treated, the air purification device being capable of decomposing, by the streamer discharge, a component to be treated which is contained in the air stream to be treated;

a concentration detector for detecting the concentration of the component to be treated which is contained in the air stream to be treated;

an air volume control part for switching the air volume of the air blower unit among a plurality of set air volume levels depending on the concentration detected by the concentration detector; and a discharge control part configured to switch the discharge electric power of the discharge device to one of a plurality of set discharge electric power levels depending on the concentration detected by the concentration detector.

4. The air purification device of claim 1 or claim 3, wherein power supply includes:

a first high voltage power supply part;

a second high voltage power supply part; and a switch for switching between the first and second high voltage power supply parts.

* * * * *